United States Patent [19]

Goldenberg

[11] 4,447,443

[45] May 8, 1984

[54] ANTI-INFLAMMATORY/ANALGESIC COMBINATION OF α-FLUOROMETHYLHISTIDINE AND A SELECTED NON-STEROIDAL ANTI-INFLAMMATORY DRUG (NSAID)

[75] Inventor: Marvin M. Goldenberg, Westfield, N.J.

[73] Assignee: Merck & Co., Inc., Rahway, N.J.

[21] Appl. No.: 441,581

[22] Filed: Nov. 15, 1982

[51] Int. Cl.³ .................... A61K 31/40; A61K 31/415
[52] U.S. Cl. ................................. 424/273 R; 424/274
[58] Field of Search ........................... 424/273 R, 274

[56] References Cited

U.S. PATENT DOCUMENTS 4,325,961  4/1982  Kollonitsch et al. ............... 424/273

OTHER PUBLICATIONS

Merck Index, 9th Edition, p. 656, Merck & Co., Inc. Rahway, N.J. (1976).

Primary Examiner—Stanley J. Friedman
Attorney, Agent, or Firm—Theresa Y. Cheng; Mario A. Monaco

[57] ABSTRACT

Combinations of α-fluoromethylhistidine and a NSAID have been found to exhibit higher efficacy and shorter onset of action in the treatment of pain and inflammation.

6 Claims, No Drawings

ANTI-INFLAMMATORY/ANALGESIC COMBINATION OF α-FLUOROMETHYLHISTIDINE AND A SELECTED NON-STEROIDAL ANTI-INFLAMMATORY DRUG (NSAID)

BACKGROUND OF THE INVENTION

This invention relates to novel pharmaceutical combinations comprising α-fluoromethylhistidine (FMH) and one or more non-steroidal anti-inflammatory/analgesic drugs (NSAID) particularly indomethacin, aspirin, diflunisal and naproxen. Unexpectedly, these novel combinations exhibit synergistic improvements over either of the separate component alone in the treatment of inflammation and pain. They are superior in terms of both more rapid onset of action and higher efficacy.

Non-narcotic analgesics, also known as non-steroidal anti-inflammatory drugs (NSAID), are widely administered orally in the treatment of mild to moderate pain. Within this class, the compounds vary widely in their chemical structure and in their biological profiles as analgesics, anti-inflammatory agents and antipyretic agents. Aspirin, acetaminophen and phenacetin have long been among the most commonly used members of this group; more recently, however, a large number of alternative non-narcotic agents offering a variety of advantages over the earlier drugs have been developed. Tolerance or addiction to these drugs is not generally a problem with their continuous use in the treatment of pain, acute or chronic inflammatory diseases, (notably, rheumatoid arthritis and osteoarthritis, dysmenorrhea); However, these new drugs generally have a higher potential for adverse side-effects. Furthermore, their effectiveness usually reaches a plateau at the upper limits of their effective dose ranges above which administration of additional drug does not increase the analgesic or anti-inflammatory effect. Among the newer compounds in the non-narcotic analgesic/non-steroidal anti-inflammatory group are compounds such as indomethacin (INDOCIN), diflunisal (DOLOBID), zomepirac sodium (ZOMAX), ibuprofen (MOTRIN), naproxen (NAPROSYN), fenoprofen (NALFON), piroxicam (FELDENE), flurbiprofen, mefenamic acid (PONSTEL) and sulindac (CLINORIL). See *Physician's Desk Reference*, 35th edition, 1981, and *The Merck Index*, 9th edition, Merck & Co., Rahway, N.J. (1976), for information on specific nonsteroidal anti-inflammatory agents.

α-Fluoromethylhistidine is a known compound being described in U.S. Pat. No. 4,325,961 issued to J. Kollonitsch et al. on Apr. 20, 1982. The compound inhibits mammalian histidine decarboxylase in vivo and thereby decreases considerably histamine levels in the body for a prolonged period.

Normally, in the classical carrageenan foot edema assay using the Sprague-Dawley male rat, (Winter et al, *Proc. Soc. Exp. Biol.*, 111, 544 1962), α-fluoromethylhistidine is ineffective in blocking inflammation induced by carrageenan although pretreatment of the rats with α-fluoromethylhistidine one and a half days prior to carrageenan significantly inhibited the hindpaw edema. However, when α-fluoromethylhistidine is used in combination with a NSAID such as indomethacin, greater anti-inflammatory effect was achieved than either agent acting alone. Such an unexpected potentiating effect was observed even at lower dose levels of both components.

Accordingly, it is the object of the present invention to provide a synergistic combination of α-fluoromethylhistidine and one or more NSAIDs for use in eliciting anti-inflammatory responses more effectively and rapidly than any of the components alone.

Another object of the invention is to provide pharmaceutical compositions for the administration of these synergistic combinations.

Still a further object of this invention is to provide an improved method of treating pain and inflammatory conditions by administering a sufficient amount of the novel combinations in a mammalian species in need of such treatment.

DETAILED DESCRIPTION OF THE INVENTION

This invention relates to synergistic combinations which elicit unexpectedly higher analgesic and/or anti-inflammatory responses at lower dose levels than possible from the individual component used alone.

The components of the combination are (A) five to 200 parts by weight of α-fluoromethylhistidine preferably 10 to 100 parts by weight and even more preferably 10 to 30 parts by weight of the structural formula:

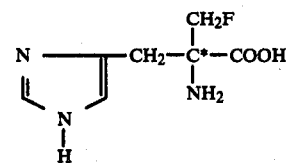

or (R)(+)-, (S)(−)-, or racemic (±)-form thereof; and (B) One part by weight of one or more non-steroidal anti-inflammatory drugs (NSAID) comprising compounds which can be categorized into five groups:

(1) the propionic acid derivatives;
(2) the acetic acid derivatives;
(3) the fenamic acid derivatives;
(4) the biphenylcarboxylic acid dervativies; and
(5) the oxicams or a pharmaceutically acceptable salt thereof.

The propionic acid derivatives which may be used comprise: ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group. Structural formulae for representative group members are set forth below:

| PROPIONIC ACID DERIVATIVES |
| --- |
| ibuprofen 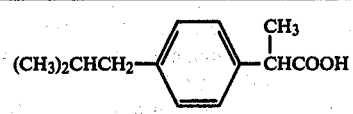 |

PROPIONIC ACID DERIVATIVES naproxen
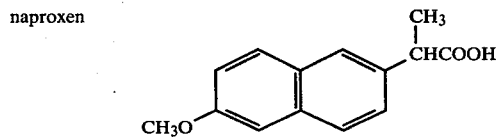

flurbiprofen
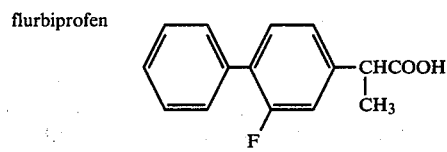

fenbufen
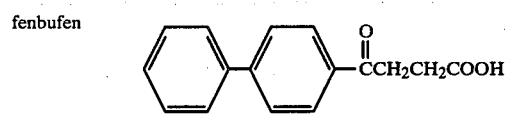

fenoprofen
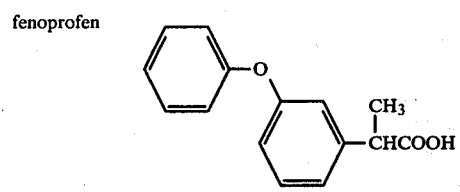

ibuprofen aluminum
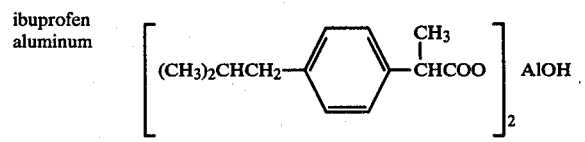

indoprofen
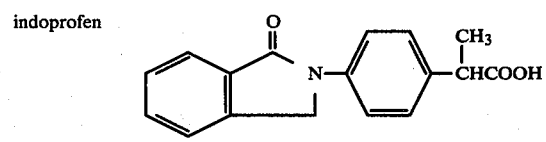

ketoprofen
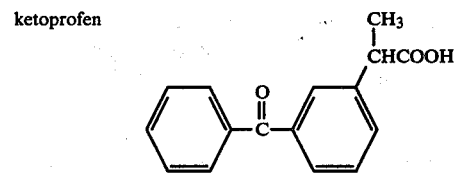

fluprofen
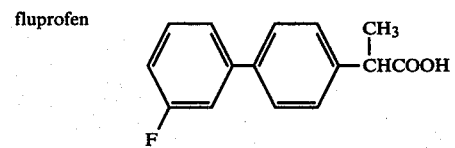

bucloxic acid
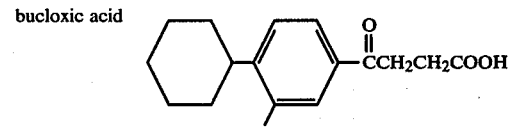

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group. Structural formulas for representative group members are set forth below:

ACETIC ACID DERIVATIVES zomepirac
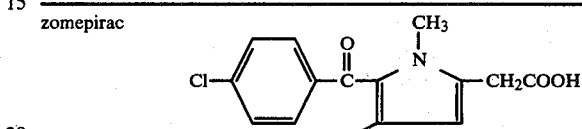

tolmetin
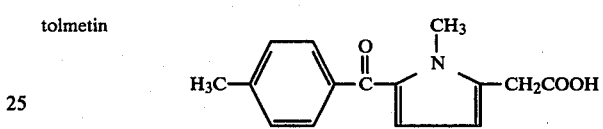

sulindac
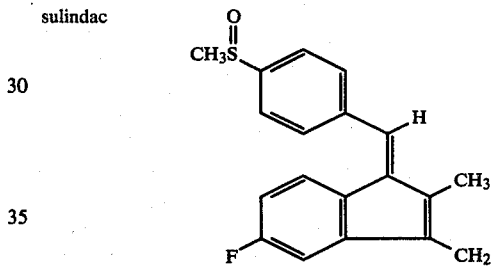

indomethacin
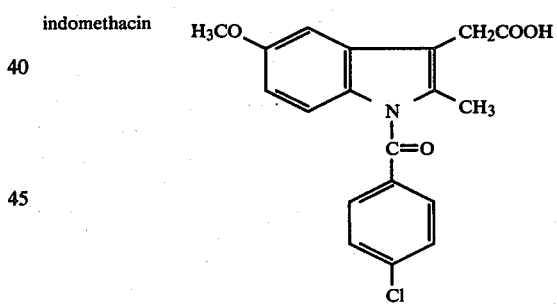

diclofenac
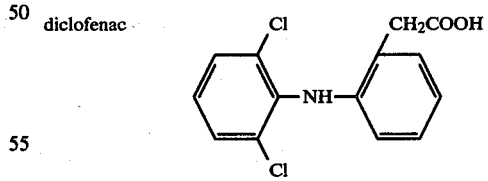

alclofenac
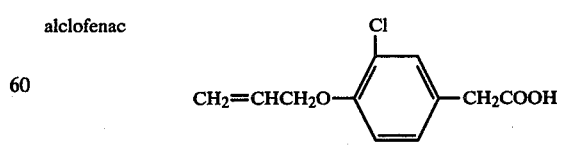

fenclozic acid
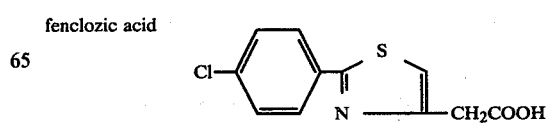

ACETIC ACID DERIVATIVES ibufenac (CH₃)₂CHCH₂—⟨C₆H₄⟩—CH₂COOH

---

Thus, "acetic acid derivatives" as defined herein are non-narcotic analgesics/nonsteroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group. Structural formulas for representative group members are set forth below:

FENAMIC ACID DERIVATIVES mefenamic acid

⟨C₆H₄(COOH)⟩—NH—⟨C₆H₃(CH₃)₂⟩ meclofenamic acid

⟨C₆H₄(COOH)⟩—NH—⟨C₆H₂(Cl)(Cl)(CH₃)⟩ flufenamic acid

⟨C₆H₄(COOH)⟩—NH—⟨C₆H₄(CF₃)⟩

---

Thus, "fenamic acid derivatives" as defined herein are non-narcotic analgesics/nonsteroidal anti-inflammatory drugs which contain the basic structure:

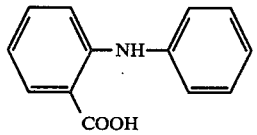

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

BIPHENYLCARBOXYLIC ACID DERIVATIVES diflunisal (structure: 2',4'-difluoro-4-hydroxybiphenyl-3-carboxylic acid, with COOH and OH on one ring, F and F on the other)

flufenisal (structure: biphenyl with OCOCH₃ and COOH on one ring, F on the other)

---

Thus, "biphenylcarboxylic acid derivatives" as defined herein are non-narcotic analgesics/non-steroidal anti-inflammatory drugs which contain the basic structure:

(biphenyl—COOH)

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group. Representative members are depicted below:

OXICAMS piroxicam (4-hydroxy-2-methyl-N-(2-pyridyl)-2H-1,2-benzothiazine-3-carboxamide 1,1-dioxide)

sudoxicam (4-hydroxy-2-methyl-N-(2-thiazolyl)-2H-1,2-benzothiazine-3-carboxamide 1,1-dioxide)

isoxicam (4-hydroxy-2-methyl-N-(5-methyl-3-isoxazolyl)-2H-1,2-benzothiazine-3-carboxamide 1,1-dioxide)

-continued

OXICAMS 4-hydroxy-1,2-benzothiazine 1,1-dioxide 4-(N—phenyl)-carboxamide

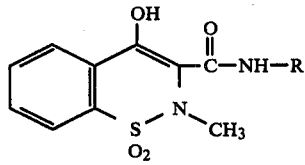

Thus, "oxicams" as defined herein are non-narcotic analgesics/nonsteroidal anti-inflammatory drugs which have the general formula:

wherein R is an aryl or heteroaryl ring system.

When a selected NSAID, for example, indomethacin, is combined with α-fluoromethylhistidine according to the present invention, the following unexpected results are obtained from the classical carrageenan foot edema assay in the Sprague-Dawley male rat following the procedures described in Winter et al, *Proc. Soc. Exp. Biol.*, 111, 544 (1962):

Protocol

Following subplantar administration of 1 mg of carrageenan in the rat hindpaw, local intense swelling, commencing the first hour, occurs over a 3-hour period. Drugs in aqueous vehicle were administered to the animals prior to the administration of carrageenan and hindpaw swelling was measured by mercury volume displacement, 1, 2 and 3 hours later. The response of drug-treated animals was compared to that of control groups receiving only aqueous vehicle. Statistically significant differences from control groups were determined using Student's "t" test.

Analysis of Results (1) Indomethacin alone

A single dose of perorally-administered indomethacin, at 3 mg/kg, significantly diminished hindpaw swelling at 1, 2 and 3 hours post carrageenan.

(2) α-Fluoromethylhistidine alone

Unlike indomethacin, one acute dose of α-FMH (50 or 100 mg/kg i.p.) was ineffective in blocking inflammation induced by carrageenan. However, pretreatment of the rat with α-FMH, 1½ days prior to carrageenan, caused inhibition of hindpaw swelling (Table 1). That is, 3 doses of α-FMH, twice on day-1 (4 hours apart) and once on day-0, at 50 or 100 mg/kg i.p., significantly inhibited edema induced by carrageenan administered on day-0, by 71% at 2 hours and 46% at 3 hours at both dose levels.

TABLE 1

Effect of Varying Dosing Regimen of α-FMH on Carrageenan Foot Edema Assay
% Inhibition of Edema at 1, 2 and 3 Hours After Challenge

| Dose Schedule | α-FMH, 50 mg/kg i.p. | | | α-FMH, 100 mg/kg i.p. | | | N |
|---|---|---|---|---|---|---|---|
| | 1 Hr. | 2 Hr. | 3 Hr. | 1 Hr. | 2 Hr. | 3 Hr. | |
| 2 × Day-1;** 1 × Day-0 | 30.6 | 73.6* | 48.3* | 19.4 | 71.8* | 46.8* | 5 |
| 1 × Day-0 | 0 | 0 | 0 | 0 | 18.3 | 13* | 5 |

(Indomethacin at 3 mg/kg p.o. given once at Day-0 inhibited edema by +20.8, 37.7% and 29% at 1, 2 and 3 hrs., respectively.)
*Statistically significant to controls at p 0.05 or less (Student's t).
**Day-1 means one day before carrageenan administration.

(3) Combination of α-fluoromethylhistidine (α-FMH) and a NSAID

Using the above-mentioned 3-dose protocol, lower dose levels of α-FMH (10 or 30 mg/kg i.p.) were combined with single doses of either indomethacin, diflunisal, or naproxen.

As shown in Table 2, a greater anti-inflammatory effect was noted at 2 and 3 hours post carrageenan when 0.3 mg/kg of indomethacin was combined with 30 mg/kg of α-FMH. At 2 hours, the combination therapy resulted in 46% inhibition of edema, while indomethacin alone or α-FMH alone resulted in only 1.8% and 13.8% inhibition, respectively. At 3 hours the combination resulted in 33.3% diminution of swelling, while indomethacin alone or α-FMH alone resulted in 8.6% and 12.4% inhibition, respectively. A more striking effect was achieved when 1 mg/kg of indomethacin was combined with 10 or 30 mg/kg of α-FMH. At 2 hours, the combination resulted in 70.6% and 61.2% inhibition, respectively, while indomethacin alone inhibited edema by 13.8% and α-FMH alone, at 10 mg/kg and 30 mg/kg, inhibited edema by +9.1% (stimulation of edema) and 13.8%, respectively.

TABLE 2

Carrageenan-Induced Foot Edema (CFE) Assay in the Rat
% Inhibition at 1, 2 and 3 Hours After Carrageenan Challenge

| | | | | | Aqueous Vehicle + α-FMH | | | | | |
|---|---|---|---|---|---|---|---|---|---|---|
| | | | | | 10 mg/kg i.p. | | | 30 mg/kg i.p. | | |
| | 1 Hr. | 2 Hr. | 3 Hr. | N | 1 Hr. | 2 Hr. | 3 Hr. | 1 Hr. | 2 Hr. | 3 Hr. |
| Aqueous vehicle i.p. + Indomethacin mg/kg p.o. | | | | | | | | | | |
| 0.3 | 0 | 1.8 | 8.6 | 5 | | | | | | |
| 1.0 | 1.7 | 13.8* | 21.2 | 5 | | | | | | |
| 3.0 | 56.5* | 42.9* | 35.1* | 5 | | | | | | |
| 0 | | | | 5 | 0 | 0 | 8.9 | 13.9 | 13.8* | 12.4* |
| Combination of both above (without aqueous vehicle) | | | | | | | | | | |
| 0.3 | | | | 5 | 0 | 0 | 0 | 0 | 45.0* | 33.3* |
| 1.0 | | | | 5 | 33.0* | 70.6* | 47.9* | 17.4 | 61.2* | 40.0* |
| 3.0 | | | | 5 | 0 | 50.9* | 49.9* | 16.5 | 37.9* | 55.8* |

Dosing Schedule
All i.p. doses, aqueous vehicle ± α-FMH given 3 ×. Two doses on Day-1, one dose on Day-0, 1 hour before carrageenan.
All p.o. doses, aqueous vehicle ± indomethacin given 1 ×, on Day-0, 1 hour before carrageenan.
*Statistically significant to controls at p 0.05 or less (Student's t).

When α-FMH was combined with diflunisal (Table 3), there was a greater effect noted at 10 and 30 mg/kg i.p. of α-FMH and 3.3 mg/kg p.o. diflunisal. The combination of 10 mg/kg α-FMH and 3.3 mg/kg diflunisal reduced inflammation by 34.6%, 24.7% and 26.2% at 1 hour, 2 hours and 3 hours respectively, after carrageenan, while 30 mg/kg α-FMH and 3.3 mg/kg diflunisal reduced inflammation by 31.3% and 30.3% at 2 hours and 3 hours post carrageenan. Used alone, neither 10 or 30 mg/kg α-FMH nor 3.3 mg/kg diflunisal reduced inflammation significantly different from the vehicle dosed control groups 1, 2 and 3 hours after carrageenan.

TABLE 3

Carrageenan-Induced Foot Edema (CFE) Assay in the Rat
% Inhibition at 1, 2 and 3 Hours

| | | | | Aqueous Vehicle + α-FMH | | | | | |
| | | | | 10 mg/kg i.p. | | | 30 mg/kg i.p. | | |
| | 1 Hr. | 2 Hr. | 3 Hr. | 1 Hr. | 2 Hr. | 3 Hr. | 1 Hr. | 2 Hr. | 3 Hr. |
|---|---|---|---|---|---|---|---|---|---|
| Aqueous vehicle i.p. + Diflunisal mg/kg p.o. | | | | | | | | | |
| 1.1 | 5.8 | +4.6 | +2.5 | | | | | | |
| 3.3 | 0 | 0 | 3.8 | | | | | | |
| 10.0 | 0 | 4.6 | 7.6 | | | | | | |
| 0 | | | | 0 | 1.6 | 1.6 | 0 | 15.9 | 16.1 |
| 1.1 | | | | 0 | 12.5 | 0 | 0 | 15.9 | 7.6 |
| 1.0 | | | | 34.6* | 24.7* | 26.2* | 0 | 31.3* | 30.3* |
| 10.0 | | | | 0 | 9.2 | 6.0 | 0 | 25.9* | 20.5* |

Dosing Schedule
α-FMH - 3 Doses: Two doses on Day-1, one dose on Day-0, 1 hour before carrageenan.
All p.o. doses, aqueous vehicle ± Diflunisal given once, on Day-0, 1 hour before carrageenan.
*Statistically significant at controls at p 0.05 or less (Student's t).

A combination of naproxen and α-FMH also appeared to cause greater reduction of inflammation in the CFE than both agents used alone. Table 4 shows that such activity was especially observed following 1.0 mg/kg p.o. of naproxen and 10 mg/kg i.p. of α-FMH. Again, at these levels, neither 10 mg/kg α-FMH nor 1.0 mg/kg naproxen reduced inflammation significantly; however, in combination, these agents reduced inflammation significantly by 35.2%, 58.1% and 49.7% at 1, 2 and 3 hours after carrageenan, respectively.

TABLE 4

Carrageenan-Induced Foot Edema (CFE) Assay in the Rat
% Inhibition at 1, 2 and 3 Hours

| | | | | Aqueous Vehicle + α-FMH | | | | | |
| | | | | 10 mg/kg i.p. | | | 30 mg/kg i.p. | | |
| | 1 Hr. | 2 Hr. | 3 Hr. | 1 Hr. | 2 Hr. | 3 Hr. | 1 Hr. | 2 Hr. | 3 Hr. |
|---|---|---|---|---|---|---|---|---|---|
| Aqueous vehicle i.p. + Naproxen mg/kg p.o. | | | | | | | | | |
| 0.33 | 6.8 | 32.8 | 35.5* | | | | | | |
| 1.0 | 9.1 | 25.3 | 21.6 | | | | | | |
| 3.0 | 11.4 | 60.7* | 65.8* | | | | | | |
| 0 | | | | 0 | 0 | 0 | 11.4 | 45.0 | 31.6 |
| 0.33 | | | | 6.8 | 0 | 2.3 | 3.4 | 11.6 | 27.4* |
| 1.0 | | | | 35.2* | 58.1* | 49.7* | 29.0* | 35.6 | 33.9* |
| 3.0 | | | | 35.2* | 39.4 | 43.2* | 33.0* | 31.8 | 55.8* |

α-FMH - 3 Doses: Two doses on Day-1, one dose on Day-0, 1 hour befor carrageenan.
All p.o. doses, aqueous vehicle ± Naproxen given once on Day-0, 1 hour before carrageenan.
*Statistically significant to controls at p 0.05 or less (Student's t).

In conclusion, the study of α-fluoromethylhistidine in the carrageenan foot edema assay has shown significant inhibition of carrageenan-induced edema when α-fluoromethylhistidine was administered i.p. three times in one and half days prior to the assay. Furthermore, the combination treatment of α-fluoromethylhistidine with a few representative NSAIDs, e.g. indomethacin, diflunisal or naproxen exerted better anti-inflammatory activity than either treatment given separately.

It has been established that most NSAIDs exhibit concurrently anti-inflammatory activity and analgesic activity. Tests for anti-inflammatory activity often also serve as good indicators for analgesic activity.

Therefore, it is well within the expectation of the present inventors that when a selected NSAID is combined with α-fluoromethylhistidine, the following results will be produced:

(1) the analgesic or anti-inflammatory effect of the selected NSAID on the mammal is brought on more quickly;

(2) lower amounts of the selected NSAID as well as α-fluoromethylhistidine are required for the same analgesic or anti-inflammatory effect; and (3) across all doses, a greater analgesic or anti-inflammatory response is achieved;

(4) fewer and less serious side effects corresponding to lower dosages would be observed.

For patients suffering inflammation and/or pain, the time from administration of medication to the onset of effective relief is clearly of paramount importance. The fact that the presently claimed combination substantially hastens the onset of analgesia and inhibition of inflammation is therefore a significant improvement.

More specifically, it is believed that approximately 3 to 5 times less of the selected NSAID can be used in the combination to achieve the same analgesic or antiinflammatory effect as that obtained by use of the selected NSAID alone; in other words, the addition of α-fluoromethylhistidine decreases the amount of the selected NSAID to about 3 to about 5 times of the usual amount to achieve the same effect. These ratios may vary, however, depending on the patient's individual response, the selected dosage level of the active ingredients etc.

For treatment of inflammation, fever or pain, the combinations of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the combinations of the present invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manfacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical composition of the present invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as solvents or suspending media. For this purpose any bland fixed oil may be employed including synthetic mono- or diglycerides. In addition, fatty acids such as oleic acid find use in the preparation of injectables.

The combinations of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The precise amount of non-narcotic analgesic/non-steroidal anti-inflammatory drug for use in the present compositions will vary depending, for example, on the specific drug chosen, the condition for which the drug is administered and the size and kind of the mammal. Generally speaking, the selected NSAID can be employed in any amount known to be an effective analgesic or anti-inflammatory amount, as well as at doses one-fifth to one-third lower than the usual amounts.

For humans, typical effective analgesic/anti-inflammatory amounts of preferred NSAIDs for use in unit dose compositions of the invention are about 50 to 150 mg indomethacin, about 125 to 1000 mg diflunisal, about 25 to 100 mg zomepirac sodium, about 400 to 2400 mg ibuprofen, about 250 to mg naproxen, about 25 to 150 mg flurbiprofen, about 50 to 400 mg fenoprofen, about 10 to 20 mg piroxicam, about 200 to 400 mg mefenamic acid, about 200 to 800 mg fenbufen or about 50 to 150 mg ketoprofen; however, greater amounts can be employed if desired. The amount of $\alpha$-fluoromethylhistidine in the combination will be an amount sufficient to shorten the onset time and/or to enhance analgesia or to reduce inflammation. However, certain NSAIDs are particularly long-acting and need be administered less frequently than the usual every 4 to 6 hours; for example, diflunisal and naproxen are typically administered only twice daily and piroxicam only once a day. When such long-acting drugs are employed, it is often necessary to include an additional amount of $\alpha$-fluoromethylhistidine in the composition in sustained release form; thus, the composition will typically contain from about 30 to about 500 (preferably about 50 to about 250) mg $\alpha$-fluoromethylhistidine for immediate release and one (or possibly more) additional dose of 30 to 500 (preferably 50 to 250) mg for sustained release. The daily dose in humans will vary with the selected NSAID, and may of course be as low as the amount contained in a single unit dose as set forth above. The daily dose for use in the treatment of mild to moderate pain will preferably not exceed 2000 mg α-fluoromethylhistidine, 250 mg indomethacin, 3000 mg diflunisal or 600 mg zomepirac sodium or 2400 mg ibuprofen or 1000 mg naproxen or 150 mg flurbiprofen or 2400 mg fenoprofen or 20 mg piroxicam or 1000 mg mefenamic acid or 2400 mg fenbufen or 300 mg ketoprofen. Greater amounts could be employed if tolerated by the patient.

What is claimed is:

1. A pharmaceutical combination for pain and anti-inflammatory management comprising a therapeutically effective amount of indomethacin or a pharmaceutically acceptable non-toxic salt thereof and α-fluoromethylhistidine in an amount sufficient to enhance the efficacy of indomethacin wherein the weight ratio of indomethacin to α-fluoromethylhistidine is from about 1:100 to about 1:3.

2. The pharmaceutical combination according to claim 1 wherein the weight ratio of indomethacin to α-fluoromethylhistidine is from about 1:30 to about 1:10.

3. A pharmaceutical composition for treatment of inflammation and pain comprising a therapeutically effective amount of indomethacin or a pharmaceutically acceptable non-toxic salt thereof and α-fluoromethylhistidine in an amount sufficient to enhance the efficacy of indomethacin and a pharmaceutically acceptable carrier wherein the weight ratio of indomethacin to α-fluoromethylhistidine is from about 1:100 to about 1:3.

4. The composition of claim 3 wherein the weight ratio of indomethacin to α-fluoromethylhistidine is from about 1:30 to about 1:10.

5. A method for treating pain and inflammation comprising administration to a patient in need of such treatment a therapeutically effective amount of indomethacin or a pharmaceutically acceptable non-toxic salt thereof and α-fluoromethylhistidine in an amount sufficient to enhance the efficacy of indomethacin wherein the weight ratio of indomethacin to α-fluoromethylhistidine is from about 1:100 to about 1:3.

6. The method according to claim 5 wherein the weight ratio of indomethacin to α-fluoromethylhistidine is from about 1:30 to about 1:10.

* * * * *